(12) United States Patent
Smith

(10) Patent No.: US 11,058,560 B1
(45) Date of Patent: Jul. 13, 2021

(54) CONNECTOR APPARATUS TO SECURE A RESIDUAL LIMB LINER TO A DISTAL PROSTHETIC MEMBER

(71) Applicant: Johan Michael Smith, Arvada, CO (US)

(72) Inventor: Johan Michael Smith, Arvada, CO (US)

( * ) Notice: Subject to any disclaimer, the term of this patent is extended or adjusted under 35 U.S.C. 154(b) by 0 days.

(21) Appl. No.: 16/808,717

(22) Filed: Mar. 4, 2020

(51) Int. Cl.
*A61F 2/78* (2006.01)
*A61F 2/80* (2006.01)

(52) U.S. Cl.
CPC .............. *A61F 2/78* (2013.01); *A61F 2/80* (2013.01); *A61F 2002/7831* (2013.01); *A61F 2002/7862* (2013.01); *A61F 2002/7875* (2013.01); *A61F 2002/7881* (2013.01)

(58) Field of Classification Search
CPC .............. A61F 2/78; A61F 2002/7831; A61F 2002/7862; A61F 2002/7875; A61F 2002/7881
See application file for complete search history.

(56) References Cited

U.S. PATENT DOCUMENTS

| 4,923,474 | A  | * | 5/1990  | Klasson ............... A61F 2/80 623/33 |
| 7,727,284 | B2 | * | 6/2010  | Warila ................ A61F 2/78 623/36 |
| 7,771,487 | B2 | * | 8/2010  | Mantelmacher ........ A61F 2/60 623/34 |
| 9,492,292 | B2 | * | 11/2016 | Mantelmacher ........ A61F 2/76 |
| 2010/0121464 | A1 | * | 5/2010 | Mantelmacher ........ A61F 2/78 623/33 |
| 2018/0008435 | A1 | * | 1/2018 | Mantelmacher ........ A61F 2/60 |

* cited by examiner

*Primary Examiner* — Bruce E Snow
(74) *Attorney, Agent, or Firm* — Plager Schack LLP; Mark H. Plager; Kara Verryt

(57) ABSTRACT

A connector apparatus for securing a liner disposed around a residual limb of a user to a distal prosthetic member is provided. The apparatus includes a body member having a roller rotatably mounted to a side wall in a slot in the body member, a socket disposed around the body member and having an opening aligned with the slot of the body member, and a strap having a first end coupled to the liner. The socket facilitates attachment of the distal prosthetic member to the body member. The strap extends through the slot in the body member against the first roller and through the opening in the socket. The strap continues to extend along an exterior surface of the socket and is attached to itself, thereby securing the liner to the distal prosthetic member.

8 Claims, 4 Drawing Sheets

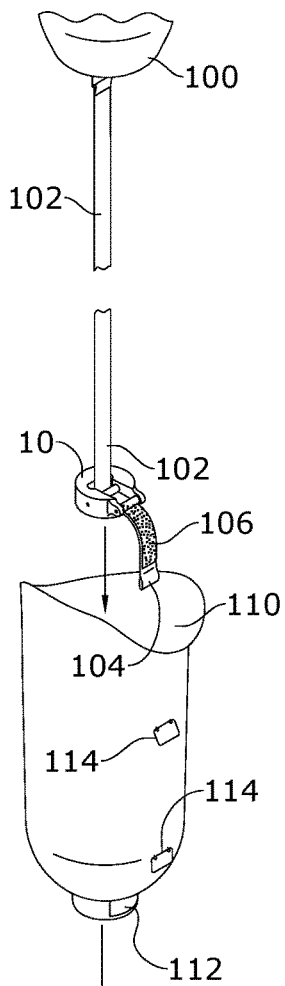
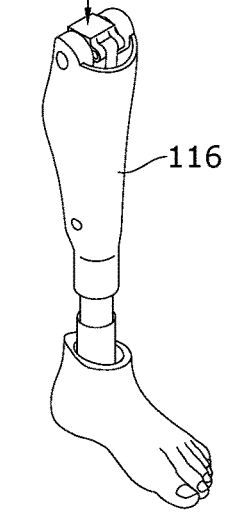
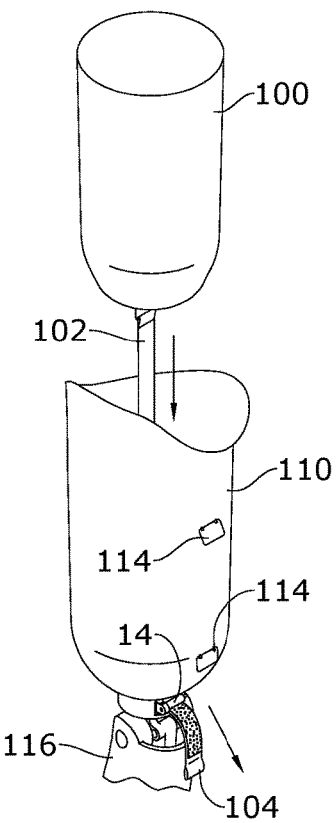
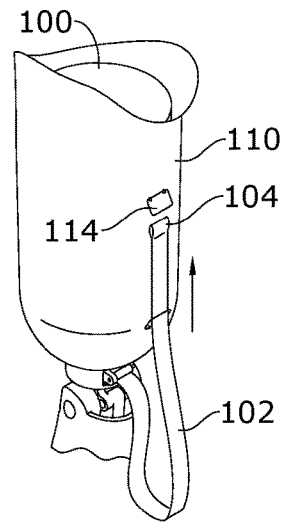
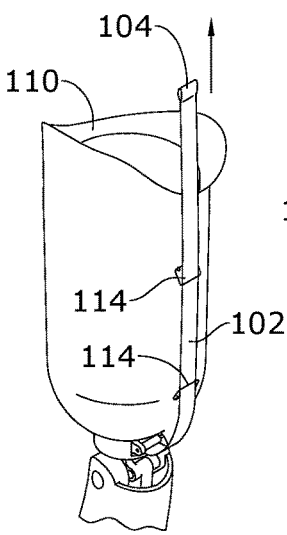
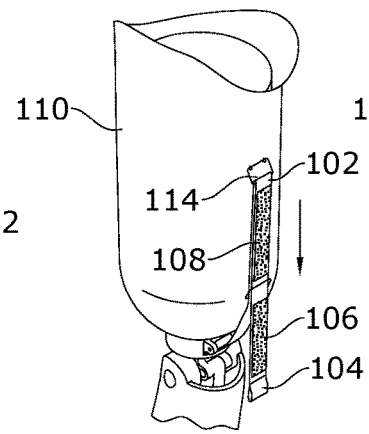
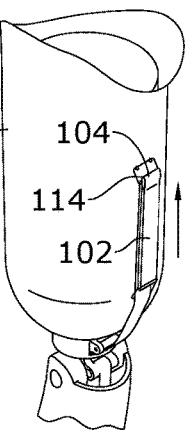
FIG.5A  FIG.5B  FIG.5C  FIG.5D  FIG.5E  FIG.5F

CONNECTOR APPARATUS TO SECURE A RESIDUAL LIMB LINER TO A DISTAL PROSTHETIC MEMBER

BACKGROUND

The embodiments herein relate generally to prosthetic members used by amputees. More specifically, embodiments of the invention are directed to a connector apparatus that secures a residual limb liner to a distal prosthetic member.

An amputee typically connects a distal prosthetic member to his/her residual limb by use of a liner and socket. The liner is commonly a silicone gel interface that is rolled over the residual limb. The residual limb and liner are placed within the socket, which is mechanically fastened to the distal prosthetic member. This installation of the liner, socket and distal prosthetic member is undesirable due to the need for mechanical fasteners, tools and/or degree of effort required to attach and detach the distal prosthetic member relative to the residual limb. In many instances, the attachment and detachment of the distal prosthetic member are difficult to perform, particularly if the amputee had an amputation on one or more of his/her upper limbs.

As such, there is a need in the industry for a connector apparatus for use to secure a liner on an amputee's residual limb to a distal prosthetic member that addresses the limitations of the prior art. Specifically, there is a need for the connector apparatus to provide a dynamic roller strap adjustment solution that allows the amputee or caregiver to secure the liner to the distal prosthetic member with enhanced efficiency and reduced effort. There is a further need for the connector apparatus to provide a connection means with enhanced strength and durability, and reduced maintenance requirements.

SUMMARY

In certain embodiments of the invention, a connector apparatus for securing a liner disposed around a residual limb of a user to a distal prosthetic member is provided. The connector apparatus is configured to provide enhanced connection strength and durability. The connector apparatus comprises a body member comprising a top face, a bottom face and a side face connecting the top and bottom faces together, the body member comprising a slot disposed therethrough and extending entirely through the top face and a portion of the side face of the body member, the body member comprising a first roller rotatably mounted to a side wall within the slot of the body member, a socket disposed around the body member and configured to house the liner, the socket comprising an opening aligned with the slot of the body member and configured to facilitate attachment of the distal prosthetic member to the body member, and a strap comprising a first end coupled to the liner and a second end, the strap extending through the slot in the body member against the first roller and through the opening in the socket, wherein the strap is configured to extend along an exterior surface of the socket and permit attachment of the second end of the strap to another portion of the strap, thereby securing the liner to the distal prosthetic member.

BRIEF DESCRIPTION OF THE FIGURES

The detailed description of some embodiments of the invention will be made below with reference to the accompanying figures, wherein the figures disclose one or more embodiments of the present invention.

FIG. 5A depicts an exploded view of certain embodiments of the connector apparatus illustrating a first step in an exemplary installation;

FIG. 5B depicts an exploded view of certain embodiments of the connector apparatus illustrating a second step in the exemplary installation;

FIG. 5C depicts an exploded view of certain embodiments of the connector apparatus illustrating a third step in the exemplary installation;

FIG. 5D depicts an exploded view of certain embodiments of the connector apparatus illustrating a fourth step in the exemplary installation;

FIG. 5E depicts an exploded view of certain embodiments of the connector apparatus illustrating a fifth step in the exemplary installation;

FIG. 5F depicts an exploded view of certain embodiments of the connector apparatus illustrating a sixth step in the exemplary installation;

DETAILED DESCRIPTION OF CERTAIN EMBODIMENTS

Figure 1:
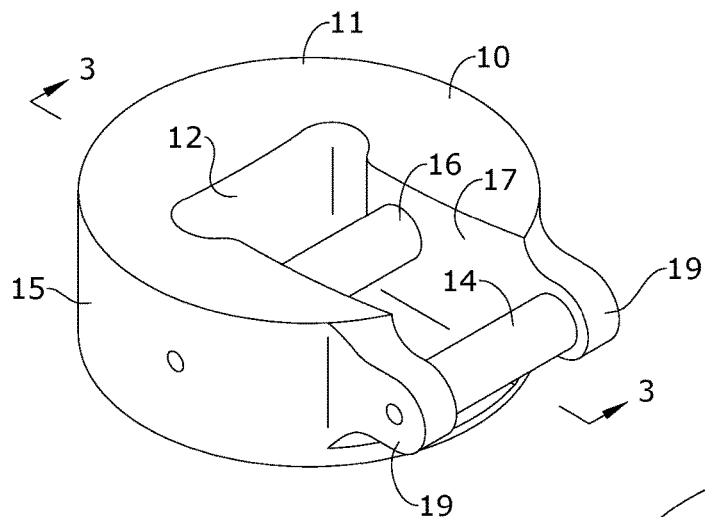
FIG. 1 depicts a top perspective view of certain embodiments of the connector apparatus.

In certain embodiments as depicted in FIGS. 1 and 5, the connector apparatus is configured to secure liner 100 to distal prosthetic member 116. The connector apparatus generally comprises body member 10, strap 102 and prosthetic socket 110. In one embodiment, liner 100 is a silicone gel interface that can be used in transfemoral, transtibial, transradial or transhumeral applications, or any other applicable amputation level that accepts a gel locking interface. In alternative embodiments, liner 100 can be made from alternative materials. Liner 100 is configured to roll over the residual limb (not shown) of the user as is known in the field.

Although the figures depict distal prosthetic member 116 for use with a user's lower residual limb, it shall be appreciated that distal prosthetic member 116 can be any type of prosthesis known in the field that is used in any of the above-mentioned applications.

In one embodiment as depicted in FIGS. 1-4, body member 10 comprises top face 11, bottom face 13, side face 15 and slot 12. Slot 12 extends entirely through top face 11 and a portion of side face 15. Slot 12 creates space within body member 10 with boundaries formed by side wall 17 and bottom face 13. In one embodiment, a pair of tabs 19 is continuously connected to body member 10 and is aligned with slot 12. Each tab 19 remains flush with side wall 17 in slot 12.

In certain embodiments, front roller 14 is rotatably mounted to the pair of tabs 19 and rear roller 16 is rotatably mounted to side wall 17. Each roller 14, 16 can be rotatably mounted to body member 10 using any components including, but not limited to, bearings, axles, fasteners or other components. In an alternative embodiment, it shall be appreciated that any alternative number of rollers can be rotatably mounted to body member 10 as desired.

Figure 2:
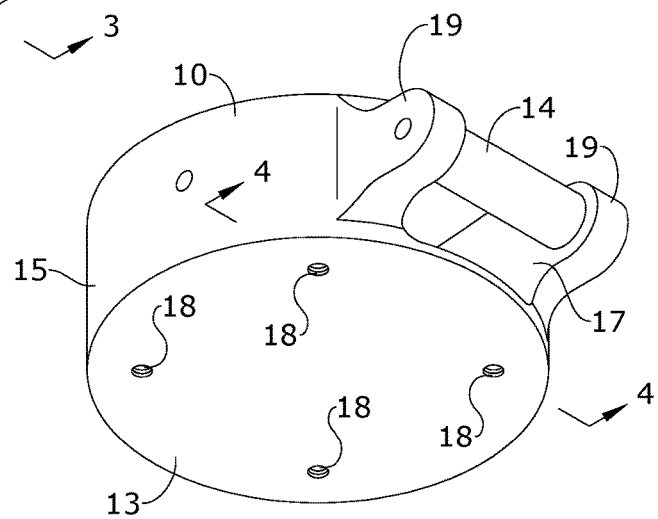
FIG. 2 depicts a bottom perspective view of certain embodiments of the connector apparatus.
Figure 3:
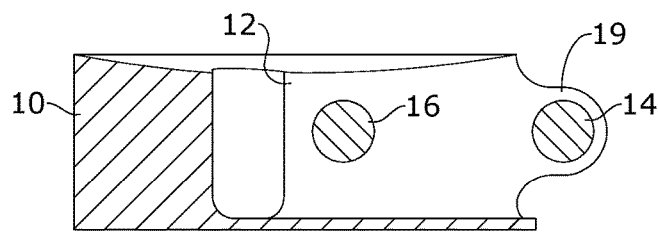
FIG. 3 depicts a section view of certain embodiments of the connector apparatus taken along line 3-3 in FIG. 1.
Figure 4:
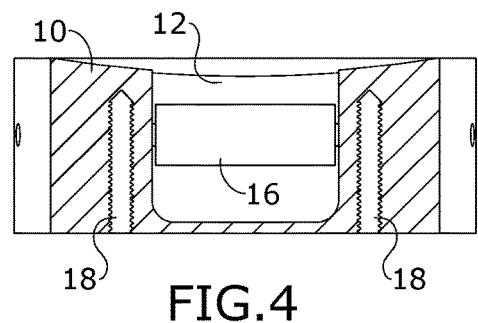
FIG. 4 depicts a section view of certain embodiments of the connector apparatus taken along line 4-4 in FIG. 2.

In one embodiment as depicted in FIGS. 2 and 4, a plurality of fastening holes 18 is disposed through bottom face 13. This allows mechanical fasteners such as screws or bolts to insert through fastening holes 18 when securing body member 10 to distal prosthetic member 116 as will be described in more detail later.

It shall be appreciated that the components of body member 10 can be made from any materials including, but not limited to, aluminum, steel, other metals, plastics, Delrin or other materials.

Figure 17:
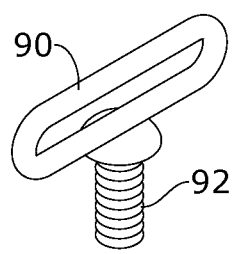
FIG. 17 depicts a perspective view of certain embodiments of the connector apparatus illustrating fastening bolt 92.

In one embodiment as depicted in FIG. 5A, the connector apparatus comprises strap 102, which comprises a first end coupled to liner 100 and a second end that is fed through slot 12 in body member 10. Strap 102 preferably is made from Dacron or a Dacron style material, nylon or other materials. In one embodiment as depicted in FIGS. 5A and 17, the first end of strap 102 is coupled to liner 100 by fastening bolt 92. Specifically, fastening bolt 92 is screwed into liner 100. The first end of strap 102 is inserted through ring 90 of fastening bolt 92 and attached thereto. It shall be appreciated that other fastening components can be used to secure strap 102 to liner 100 in alternative embodiments.

In one embodiment as depicted in FIGS. 5A and 5E, the second end of strap 102 comprises strap loop 104. A fastener is coupled to strap 102 to permit the second end of strap 102 to fasten to itself. In one embodiment, the fastener comprises hook fastening strip 106 and loop fastening strip 108 coupled to strap 102 proximate the second end. The second end of strap 102 is configured to fold onto an intermediate portion of the strap to permit hook fastening strip 106 and loop fastening strip 108 to engage with each other. It shall be appreciated that the locations of hook and loop fastening strips 106, 108 on strap 102 can be swapped or moved to alternate locations on the strap. In an alternative embodiment, strap 102 can have alternative fastening components such as snap components, laces, strings or other fasteners.

In one embodiment as depicted in FIG. 5, the connector apparatus comprises prosthetic socket 110, which is configured to receive body member 10, strap 102, liner 100 and the residual limb of the user. Prosthetic socket 110 preferably is made from thermoforming plastics and/or laminated acrylic resins. However, it shall be appreciated that prosthetic socket 110 can be made from alternative materials. In one embodiment, prosthetic socket 110 comprises strap opening 112 and a pair of attachment members on the exterior surface such as guide rings 114.

In operation, the connector apparatus is coupled to liner 100 and distal prosthetic member 116. The following exemplary steps are performed in certain embodiments of the invention. Liner 100 is disposed over the residual limb of the user. As depicted in FIG. 5A, the first end of strap 102 is coupled to liner 100 and the remaining portion of the strap is fed through slot 12 in body member 10 so that strap loop 104 extends outside of body member 10. As depicted in FIGS. 5A-5B, body member 10 is lowered to the bottom of prosthetic socket 110 so that slot 12 of body member 10 is aligned with strap opening 112 in prosthetic socket 110. Strap loop 104 is pulled to extend through strap opening 112 and outside of prosthetic socket 110.

In one embodiment, body member 10 is coupled to distal prosthetic member 116 using any brackets, screws or other mechanical fasteners. In one embodiment, a plurality of screws couple distal prosthetic member 116 to body member 10 by extending through prosthetic socket 110 and fastening holes 18 in body member 10.

In one embodiment as depicted in FIGS. 5C-5D, strap 102 is pulled upward and fed through the pair of guide rings 114 on prosthetic socket 110. In one embodiment as depicted in FIG. 5E, strap 102 is pulled downward and fed through the pair of guide rings 114 on prosthetic socket 110. In one embodiment as depicted in FIG. 5F, strap loop 104 of strap 102 is folded onto an intermediate portion of the strap to permit hook fastening strip 106 and loop fastening strip 108 to engage with each other. This tightly secures liner 100 to distal prosthetic member 116. In this assembly, liner 100 sits on body member 10 within prosthetic socket 110 when the liner is secured to the distal prosthetic member. To detach distal prosthetic member 116 from liner 100, strap 102 is detached from itself and fed through strap opening 112 in prosthetic socket 110 and body member 10 in the reverse direction.

As such, body member 10 serves as a central connection point that connects liner 100 to distal prosthetic member 116. As strap 102 is pulled or retracted through body member 10, front and rear rollers 14, 16 of body member 10 contact strap 102 and facilitate the movement of strap 102 with minimal user effort.

Figure 15:
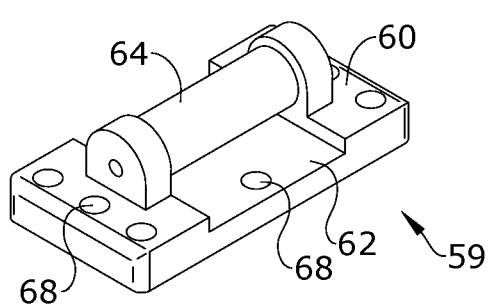
FIG. 15 depicts a top perspective view of certain embodiments of the connector apparatus illustrating an attachment member.
Figure 16:
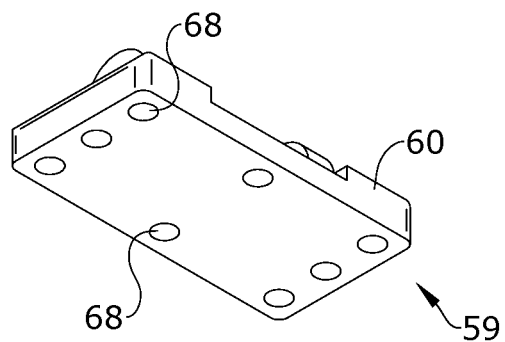
FIG. 16 depicts a bottom perspective view of certain embodiments of the connector apparatus illustrating the attachment member.

In an alternative embodiment as depicted in FIGS. 15-16, alternate attachment members 59 are coupled to prosthetic socket 110 instead of guide rings 114. In one embodiment, alternate attachment member 59 comprises bar 64 rotatably mounted to base member 60. Strap slot 62 between bar 64 and base member 60 is sufficiently large to permit strap 102 to pass therethrough. Base member 60 of each alternate attachment member 59 comprises a plurality of openings 68 configured to receive fasteners to permit the attachment of alternate attachment member 59 to prosthetic socket 110.

Alternate attachment members 59 are advantageous because rotatable bars 64 facilitate the movement of strap 102 while minimizing wear on the strap. Bars 64 also reduce user effort when maneuvering strap 102 through body member 10. The components of alternate attachment members 59 can be made from materials including, but not limited to, aluminum, steel, other metals, plastics, Delrin or other materials.

Figure 6:
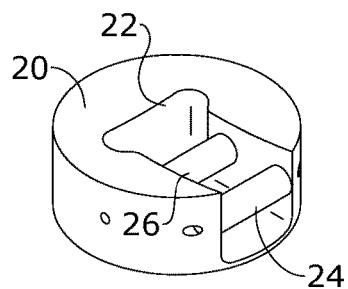
FIG. 6 depicts a top perspective view of certain embodiments of the connector apparatus illustrating first alternate body member 20.
Figure 7:
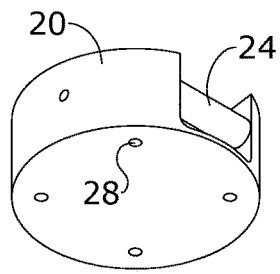
FIG. 7 depicts a bottom perspective view of certain embodiments of the connector apparatus illustrating first alternate body member 20.

It shall be appreciated that connector body 10 can have modifications in size, shape and number of fastening holes to accommodate the user, liner and/or distal prosthetic member. In one embodiment as depicted in FIGS. 6-7, first alternate body member 20 comprises first alternate slot 22, first alternate front roller 24, first alternate rear roller 26 and first alternate fastening holes 28. First alternate body member 20 is made from the same materials and is used in the same manner as body member 10.

Figure 8:
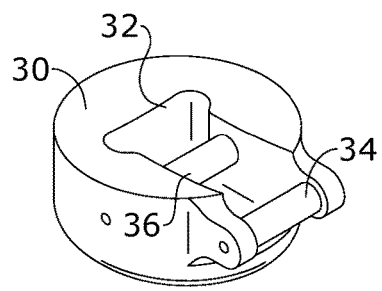
FIG. 8 depicts a top perspective view of certain embodiments of the connector apparatus illustrating second alternate body member 30.
Figure 9:
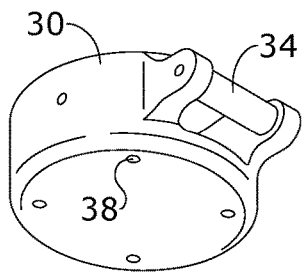
FIG. 9 depicts a bottom perspective view of certain embodiments of the connector apparatus illustrating second alternate body member 30.
Figure 10:
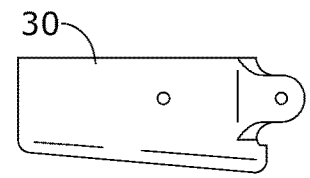
FIG. 10 depicts a side view of certain embodiments of the connector apparatus illustrating second alternate body member 30.

In one embodiment as depicted in FIGS. 8-10, second alternate body member 30 comprises second alternate slot 32, second alternate front roller 34, second alternate rear roller 36 and second alternate fastening holes 38. In one embodiment as depicted in FIG. 10, the bottom face of second alternate body member 30 is slanted and extends within the approximate range of 5-15 degrees relative to the horizontal plane. This slanted surface on second alternate body member 30 provides preflexion for alignment possibilities with different distal prosthetic members 116. Second alternate body member 30 is made from the same materials and is used in the same manner as body member 10.

Figure 11:
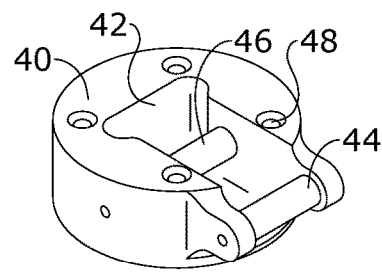
FIG. 11 depicts a top perspective view of certain embodiments of the connector apparatus illustrating third alternate body member 40.
Figure 12:
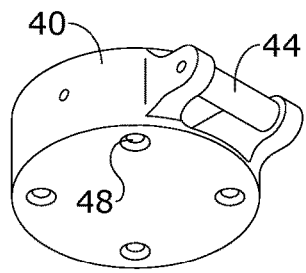
FIG. 12 depicts a bottom perspective view of certain embodiments of the connector apparatus illustrating third alternate body member 40.

In one embodiment as depicted in FIGS. 11-12, third alternate body member 40 comprises third alternate slot 42, third alternate front roller 44, third alternate rear roller 46 and third alternate fastening holes 48. Third alternate body member 40 is made from the same materials and is used in the same manner as body member 10.

Figure 13:
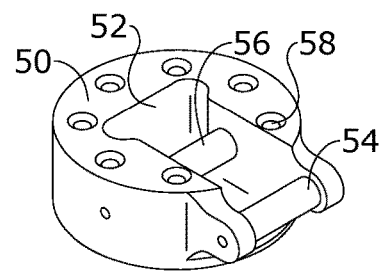
FIG. 13 depicts a top perspective view of certain embodiments of the connector apparatus illustrating fourth alternate body member 50.
Figure 14:
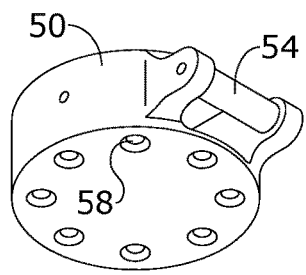
FIG. 14 depicts a bottom perspective view of certain embodiments of the connector apparatus illustrating fourth alternate body member 50.

In one embodiment as depicted in FIGS. 13-14, fourth alternate body member 50 comprises fourth alternate slot 52, fourth alternate front roller 54, fourth alternate rear roller 56 and fourth alternate fastening holes 58. Fourth alternate body member 50 is made from the same materials and is used in the same manner as body member 10.

It shall be appreciated that the components of the connector apparatus described in several embodiments herein may comprise any alternative known materials in the field and be of any color, size and/or dimensions. It shall be appreciated that the components of the connector apparatus described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention, the scope of the invention is reflected by the breadth of the claims below rather than narrowed by the embodiments described above.

What is claimed is:

1. A connector apparatus for securing a liner disposed around a residual limb of a user to a distal prosthetic member, the connector apparatus configured to provide enhanced connection strength and durability, the connector apparatus comprising:
    a body member comprising a top face, a bottom face and a side face connecting the top and bottom faces together, the body member comprising a slot disposed therethrough and extending entirely through the top face and a portion of the side face of the body member, the body member comprising a first roller rotatably mounted to a side wall within the slot of the body member;
    a socket disposed around the body member and configured to house the liner, the socket comprising an opening aligned with the slot of the body member and configured to facilitate attachment of the distal prosthetic member to the body member;
    a strap comprising a first end coupled to the liner and a second end, the strap extending through the slot in the body member against the first roller and through the opening in the socket, wherein the strap is configured to extend along an exterior surface of the socket and permit attachment of the second end of the strap to another portion of the strap, thereby securing the liner to the distal prosthetic member;
    a second roller rotatably mounted to the side wall in the slot of the body member and in contact with the strap, wherein:
        the liner sits on the body member within the socket when the liner is secured to the distal prosthetic member.

2. The connector apparatus of claim 1, further comprising a pair of tabs continuously connected to the body member, each tab in the pair of tabs being an extension of the side wall in the slot of the body member,
    wherein the second roller is rotatably mounted to the pair of tabs.

3. The connector apparatus of claim 2, further comprising a pair of attachment members coupled to the exterior surface of the socket, the pair of attachment members configured to permit the strap to pass therethrough as it extends along the exterior surface of the socket.

4. The connector apparatus of claim 3, further comprising a fastener coupled to the strap and configured to permit the second end of the strap to couple to the another portion of the strap.

5. The connector apparatus of claim 4, wherein each attachment member in the pair of attachment members comprises a guide ring that permits the strap to pass therethrough.

6. The connector apparatus of claim 4, wherein each attachment member in the pair of attachment members comprises a base member and a bar rotatably mounted to the base member, the attachment member configured to permit the strap to extend therethrough between the base member and bar.

7. The connector apparatus of claim 6, wherein the base member in each attachment member in the pair of attachment members is mechanically coupled to the socket.

8. The connector apparatus of claim 7, wherein the body member is mechanically coupled to the distal prosthetic member.

* * * * *